(12) United States Patent
Herbig et al.

(10) Patent No.: US 6,562,583 B1
(45) Date of Patent: May 13, 2003

(54) METHOD FOR DETECTING MICROORGANISMS IN GASES

(75) Inventors: Elmar Herbig, Göttingen (DE); Dietmar Nussbaumer, Göttingen (DE); Khuong To Vinh, Bockenem (DE)

(73) Assignee: Sartorius AG, Goettingen (DE)

( * ) Notice: Subject to any disclaimer, the term of this patent is extended or adjusted under 35 U.S.C. 154(b) by 407 days.

(21) Appl. No.: 09/635,712

(22) Filed: Aug. 9, 2000

Related U.S. Application Data

(63) Continuation of application No. PCT/EP99/02194, filed on Mar. 30, 1999.

(30) Foreign Application Priority Data

Apr. 2, 1998 (DE) .......................... 198 14 715

(51) Int. Cl.[7] .............................. C12Q 1/04; C12Q 1/37; G01N 33/53
(52) U.S. Cl. ..................... 435/34; 435/23; 435/836; 435/968
(58) Field of Search ............................ 435/34, 23, 836, 435/968

(56) References Cited

U.S. PATENT DOCUMENTS 5,498,526 A * 3/1996 Caputo et al. ................. 435/31
5,739,004 A * 4/1998 Woodson ....................... 435/31

FOREIGN PATENT DOCUMENTS

| DE | 11 73 640 B | 5/1959 |
| DE | 197 50 215 C | 2/1999 |
| WO | 89 08834 A | 9/1989 |

* cited by examiner

*Primary Examiner*—Louise N. Leary
(74) *Attorney, Agent, or Firm*—Chernoff, Vilhauer, McClung & Stenzel, LLC

(57) ABSTRACT

A method of conducting a rapid microbiological assay of gases is disclosed that utilizes an improved gelatin membrane filter that is pre-filtered before casting to remove microscopic-sized particles.

12 Claims, No Drawings

METHOD FOR DETECTING MICROORGANISMS IN GASES

This application is a continuation of PCT/EP99/02194, filed Mar. 30, 1999, and claims priority to DE 198-14715.5, filed Apr. 2, 1998.

BACKGROUND OF THE INVENTION

In certain spaces with special requirements for the state of the air, such as in air-conditioned rooms, clean rooms and isolation areas, the air is regularly analyzed as to its microbial content. Since filtered air generally is involved, which tends to exhibit a low microbial content, large volumes are usually tested in order to collect sufficient microorganisms for a representative test result. To that end an air sample is typically collected by an air collection apparatus, such as is marketed by the firm Sartorius under the name MD8 air scan and filtered through an appropriate filter. Filters employed for this purpose are sterile membrane filters with pore sizes as prescribed in microfiltration technology, predominately of gelatin. See, for example, DE PS 11 73 640. Such gelatin membrane filters retain microorganisms and hold them in a moist and reproductive condition. Following the sampling, the gelatin membrane filters can be incubated on an agar culture medium whereby, from the individually collected microorganism aggregates, colonies are grown; the gelatin filter liquefies and disappears so as to permit the microorganism colonies to be counted directly on the agar. In another alternate method, the gelatin filter can be dissolved in a sterile solution, such as a peptone solution of water or an isotonic salt solution, so that representative quantities can be incubated on various culture media. In any case, in accord with these procedures, the analysis results are received long after the fact, since the typical microbial colony growth rate is on the order of seven days.

A much more rapid microbiological assay, known as ChemScan® is theoretically available for use with such gelatin-based filters, allowing a representative microbial count within 30 to 90 minutes. For this type of analysis an aqueous sample containing the living microorganisms would be filtered through a 0.22 $\mu$m or a 0.45 $\mu$m analysis membrane in order to retain the microorganisms captured by the gelatin membrane filter. The analysis membrane would then be laid upon an absorption substrate for 30 minutes at 30° C. and saturated with an enzymatic marking fluid. The marking fluid is capable of causing enzyme-activated interaction with the microorganisms' cell cytoplasm, ideally yielding a yellow fluorescence. Finally, by means of a microscope, preferably with a laser scan, individual microorganisms on the analysis membrane should be detectable by virtue of their fluorescence. Just as in the case of conventional assays, such a rapid microbiological assay may convert the microorganism-containing gelatin filter to a test sample by dissolving the gelatin filter in an aqueous solution such as an aqueous peptone solution. Unfortunately, attempts to conduct such a rapid assay conducted with conventional gelatin membranes have not yielded an observable yellow fluorescence on the analysis membrane as the analysis membrane remains red-colored throughout the procedure.

Thus the invention has the object of providing a procedure for a rapid assay of microorganisms and to that end the related object of providing suitable gelatin membrane filters for use in such rapid assays. These objects and others which will become apparent to one of ordinary skill in the art are summarized and described in detail below.

BRIEF SUMMARY OF THE INVENTION

The essence of the present invention lies in the discovery that gelatin membranes that are free from microscopic particles greater than 0.45 $\mu$m in diameter provide vastly superior microorganism-collecting membrane filters for purposes of utilizing the latest rapid microbiological assay method noted above.

The invention also provides a method for rapid and near real time determination of microorganisms in gases, comprising the following steps:

(a) providing a gelatin membrane filter free of particles greater than 0.45 $\mu$m in diameter;

(b) forming a membrane containing microorganisms by contacting the membrane of step (a) with a gas containing microorganisms;

(c) forming a solution containing the membrane-captured microorganisms by dissolving the membrane containing microorganisms of step (b) in an aqueous solution containing an enzymatic marking substance which causes the microorganisms to fluoresce;

(d) collecting flourescent microorganisms by filtering the solution of step (c) through an analysis membrane having a pore size of from about 0.2 to about 0.45 $\mu$m; and (e) counting the fluorescent microorganisms of step (d).

The method can be used for the determination of microorganisms in gaseous media, especially air, in pharmaceutical, biotechnical, and food industries. Further, application is found in environmental operations, in waste industries, and in medical apparatus for the determination of germ contamination of the gaseous media. The gelatin membrane filters, in accord with the invention, may be used in combination with a collection device for the capture of bacteria, spores, viruses, yeasts and microorganisms to determine the degree of germ contamination in a given space.

DETAILED DESCRIPTION OF PREFERRED EMBODIMENTS

According to the present invention there are provided gelatin membranes that are free from microorganisms, including dead microorganisms. Rather surprisingly, it has been discovered that the use of gelatin freed from microscopic particles as a starting material for the manufacture of a gelatin membrane filter provides a superior microorganism-capturing filter. To this end, a casting solution of commercial gelatin is first filtered under pressure through a microfiltration membrane having a pore size diameter of up to about 0.45 $\mu$m, preferably up to about 0.2 $\mu$m, and most preferably up to 0.1 $\mu$m. A hydrophilic, cross-linked, 0.2 $\mu$m cellulose hydrate membrane has proven itself as especially appropriate as such a microfiltration membrane, commercially available as Hydrosart®, from Sartorius AG of Gottingen, Germany. By such pre-filtration of the gelatin from which the membrane filters are cast, all particles of the stated size are removed from all the components of the membrane casting solution in a single step. Pressure filtration is preferable as compared to vacuum filtration, since volatile solvents cannot vaporize and the composition of the membrane casting solution is not altered.

A commercial gelatin membrane filter available from ChemScan® made and sterilized directly, without the inventive pre-filtration step can contain between about 10,000 and 1,000,000 dead microorganisms per gram. Such microorganism counts are obviously responsible for the failure of fluorescent marking of membrane filters in the rapid test procedures employed in the ChemScan® process inasmuch as microorganisms, especially dead microorganisms, cause a red coloration in the analysis membrane, thereby preventing detection of the fluorescence of living microorganisms.

The gelatin membrane filters in accord with the invention are well adapted in particular for rapid microbiological assays for the direct determination of individual microorganisms, in particular living microorganisms, which may be identified by fluorescence. The gelatin membrane filter upon which microorganisms have been captured is dissolved in an aqueous solution, filtered through an analysis membrane with pore sizes ranging from about 0.2 μm to 0.45 μm, in order to collect the microorganisms. For this step micro-sieve membranes are preferred, as described in WO 95/13860 A1, especially nuclear track etched membranes with pore diameters of about 0.2 μm, as they have a narrow pore size distribution and because of the abundance of pore openings perpendicular to the membrane surface, which permit high filtration rates. They are also preferred because microorganisms are retained completely on the surface of the membranes and not, as is the case with conventional membranes, inside the pore structure of the membrane. The analysis membrane may then be placed for, say, 30 minutes at 300° C. on an absorptive substrate and then impregnated with an enzymatic marking agent to induce fluorescence in the microorganisms. In a preferred embodiment, the marking agent is added directly to the aqueous solution used to dissolve the gelatin membrane filter and after a time adequate for the enzymatic reaction to take place, the now tagged microorganisms are collected on the analysis membrane. Finally, individual fluorescing microorganisms are counted under a microscope, preferably with a laser-scan system.

A preferred procedure for the manufacture of the gelatin membrane filter in accord with the invention is carried out as follows. With the exception of the addition of an osmoprotective agent, all percentages noted for the components of the casting solution are expressed as weight percentages based on the total membrane casting solution. A homogeneous aqueous membrane casting solution comprising 4.5 to 5.6% gelatin, 38 to 46% ethanol, and optionally 0.02 to 0.1% binder such as polyvinyl alcohol. In a preferred embodiment, in order to markedly enhance the viability of live microorganisms collected on the gelatin membrane, the membrane casting solution is then doped with 0.005 to 0.75% of at least one osmoprotective agent relative to the gelatin content; trimethylammonioaceate is an appropriate and preferred osmoprotective agent. This membrane casting solution is filtered under a pressure differential ranging from 2 to 5 bar, preferably 3 bar, through a microfiltration membrane having maximum pore diameters of 0.4 μm, preferably 0.2 μm. Next a thin film of the membrane casting solution is spread on a substrate and the thin film so formed is allowed to air dry to form a gelled phase. The gelled phase is then cured in a precipitation bath of methyl acetate.

In a further embodiment of the invention, two precipitation baths are used. The first bath comprises methyl acetate with an alcohol, preferably methanol, those two components comprising 10 to 20 wt % of the entire contents of the first bath. The membrane remains in this first bath for a period of time of from one to three hours at room temperature before it is transferred to a second precipitation bath comprising pure methyl acetate. The final two steps in forming the gelatin membrane filter comprise drying and sterilizing, the latter preferably by gamma rays.

EXAMPLE

Two hundred grams of commercial gelatin powder and 2 g polyvinyl alcohol as a binding agent were dissolved in 2000 g water during constant mixing at 60° C., and subsequently mixed with 1645 g ethanol and 0.02 g trimethylammonioacetate in 10 g water as an osmoprotective agent. This membrane casting solution was filtered in a dead end filtration module at a pressure differential of 3 bar and a temperature of about 40° C. through a crosslinked cellulose hydrate membrane with pore sizes 0.2 μm in diameter. The filtered membrane casting solution was cooled to 21° C. and spread in a film 350 μm thick on a substrate and exposed to air at room temperature with a relative humidity of 45% for about 5 minutes. The gelled film and substrate were then placed into a first precipitation bath comprising methyl acetate and 14 wt % methanol for 3 hours. The film and substrate were then deposited in a second precipitation bath of pure methyl acetate for another 3 hours. The gelatin membrane filter was then peeled from the substrate, dried and sterilized with gamma rays. The gelatin membrane filter so obtained exhibited an air flux of 140 L/m.cm⁻n.bar.

The membrane filter containing 150 mg gelatin was dissolved in 50 mL peptone water and treated with 100 μl of an alkaline protease enzyme derived from *Bacillus licheniformis* fluorescence in the microorganisms; the enzyme is commercially available as Delvolase from DSM Food Specialties of Dortmund, Germany. After incubation for 5 minutes at 37° C. the solution was filtered through a 0.4 μm analysis membrane of cellulose nitrate followed by examination of the analysis membrane under a microscope. No microorganisms were detected.

Comparative Example

The Example noted above was repeated except there was no filtration of the membrane casting solution prior to casting. After treatment with Delvolase®, examination of the analysis membrane exhibited a uniform red color, indicating the presence of a multiplicity of microorganisms.

As is apparent, the present invention dispenses with the one week incubation period required in conventional microbiological assays and permits rapid, near real time assays, making the membrane filters and the method particularly suitable for quality control applications in the pharmaceutical and biotechnology fields.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A method for determining the presence of microorganisms in gases comprising the following steps:
   (a) providing a gelatin membrane filter free of particles greater than 0.45 μm in diameter;
   (b) forming a membrane containing microorganisms by contacting said membrane of step (a) with a gas containing microorganisms;
   (c) forming a solution containing said microorganisms by dissolving said membrane containing microorganisms of step (b) in an aqueous solution containing an enzymatic marking substance which causes said microorganisms to fluoresce;
   (d) collecting flourescent microorganisms by filtering said solution of step (c) through an analysis membrane having a pore size of from about 0.2 to about 0.45 μm; and
   (e) counting said fluorescent microorganisms of step (d).

2. The method of claim 1 wherein said gelatin membrane filter of step (a) is free of particles greater than 0.1 µm in diameter.

3. A method of making a gelatin membrane filter comprising the steps:
   (a) forming an aqueous homogenous membrane casting solution of 4.5 to 5.6 wt % gelatin and 38 to 46 wt % ethanol;
   (b) forming a filtered casting solution by filtering said casting solution of step (a) through a microfiltration membrane having pores of up to 0.45 µm in diameter;
   (c) forming a cast film by spreading a thin film of said filtered membrane casting solution of step (b) on a substrate;
   (d) forming a gelled cast film by exposing said cast film of step (c) to air;
   (e) forming a gelatin membrane filter by immersing said gelled cast film of step (d) in a bath comprising methyl acetate;
   (f) drying said gelatin membrane filter of step (e).

4. The method of claim 3, wherein step (a) includes the addition of 0.005 to 0.75 wt % osmoprotective agent relative to the gelatin content of said casting solution.

5. The method of claim 4 wherein said osmoprotective agent is trimethylammonioacetate.

6. The method of claim 3 wherein step (a) includes the addition of 0.02 to 0.1 wt % binding agent.

7. The method of claim 6 wherein said binding agent comprises polyvinyl alcohol.

8. The method of claim 3 wherein step (b) is conducted under a pressure differential of from 2 to 5 bar.

9. The method of claim 8 wherein step (b) is conducted with a microfiltration membrane having pores of up to 0.1 µm in diameter.

10. The method of claim 3 wherein the bath of step (e) comprises 10 to 20 wt % methanol.

11. The method of claim 10 including immersing said cast film in a second bath comprising substantially pure methyl acetate.

12. The product of the method of any of claims 3–11.

* * * * *

UNITED STATES PATENT AND TRADEMARK OFFICE
CERTIFICATE OF CORRECTION

PATENT NO. : 6,562,583 B1
DATED : May 13, 2003
INVENTOR(S) : Herbig, Nussbaummer and To Vinh It is certified that error appears in the above-identified patent and that said Letters Patent is hereby corrected as shown below:

<u>Column 3,</u>
Line 45, delete "trimethylammonioacetate" and substitute therefore
-- trimethylammonium acetate --.

<u>Column 4,</u>
Line 18, delete "140 L/m.cm⁻n.bar." and substitute therefore -- L/m•m²•bar. --.

Signed and Sealed this

Fifteenth Day of July, 2003

JAMES E. ROGAN
*Director of the United States Patent and Trademark Office*